(12) United States Patent
Pham et al.

(10) Patent No.: US 6,903,063 B2
(45) Date of Patent: Jun. 7, 2005

(54) AZEOTROPE-LIKE COMPOSITION OF 1-CHLORO-1,3,3,3-TETRAFLUOROPROPANE AND HYDROGEN FLUORIDE

(75) Inventors: Hang Thanh Pham, Erie County, NY (US); Rajiv Ratna Singh, Erie County, NY (US); Hsueh Sung Tung, Erie County, NY (US); Milton Cook, Niagara County, NY (US)

(73) Assignee: Honeywell International Inc., Morristown, NJ (US)

( * ) Notice: Subject to any disclaimer, the term of this patent is extended or adjusted under 35 U.S.C. 154(b) by 192 days.

(21) Appl. No.: 10/283,400

(22) Filed: Oct. 29, 2002

(65) Prior Publication Data

US 2003/0096724 A1 May 22, 2003

Related U.S. Application Data

(62) Division of application No. 09/768,416, filed on Jan. 24, 2001, now Pat. No. 6,500,795.

(51) Int. Cl.$^7$ ................................................ C11D 7/30
(52) U.S. Cl. ...................... 510/408; 510/411; 252/67; 252/364
(58) Field of Search ............................. 510/408, 411, 510/177; 252/67, 364; 570/168

(56) References Cited

U.S. PATENT DOCUMENTS

| | | | |
|---|---|---|---|
| 5,496,866 A | 3/1996 | Sommerfeld et al. | 521/131 |
| 5,574,192 A | 11/1996 | VanDerPuy et al. | 570/167 |
| 6,291,730 B1 | 9/2001 | Baker et al. | 570/176 |
| 6,500,795 B2 * | 12/2002 | Pham et al. | 510/412 |
| 6,534,467 B2 * | 3/2003 | Pham et al. | 510/408 |
| 6,759,381 B1 * | 7/2004 | Johnson et al. | 510/408 |

* cited by examiner

*Primary Examiner*—Gregory Webb
(74) *Attorney, Agent, or Firm*—Honeywell International Inc.

(57) ABSTRACT

The invention relates to azeotropic and azeotrope-like mixtures of 1-chloro-1,3,3,3-tetrafluoropropane (HCFC-244fa) and hydrogen fluoride, which are useful as intermediates in the production of HCFC-244fa.

15 Claims, 2 Drawing Sheets

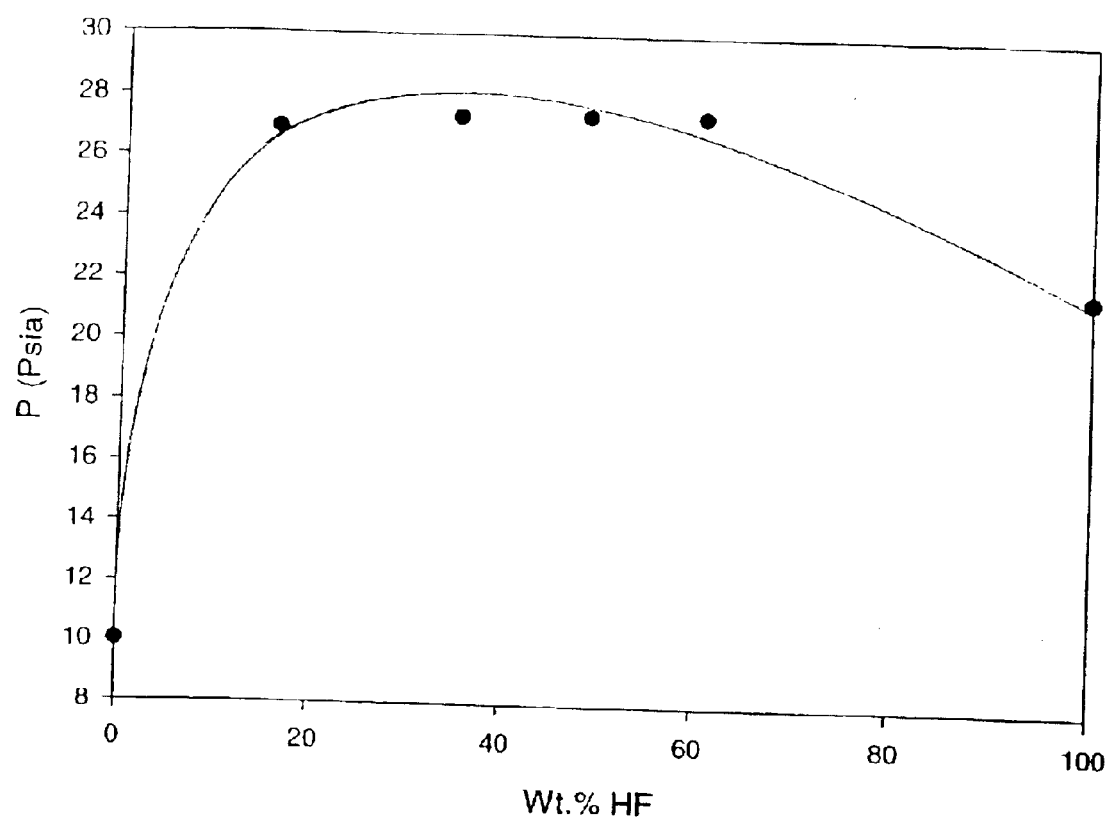

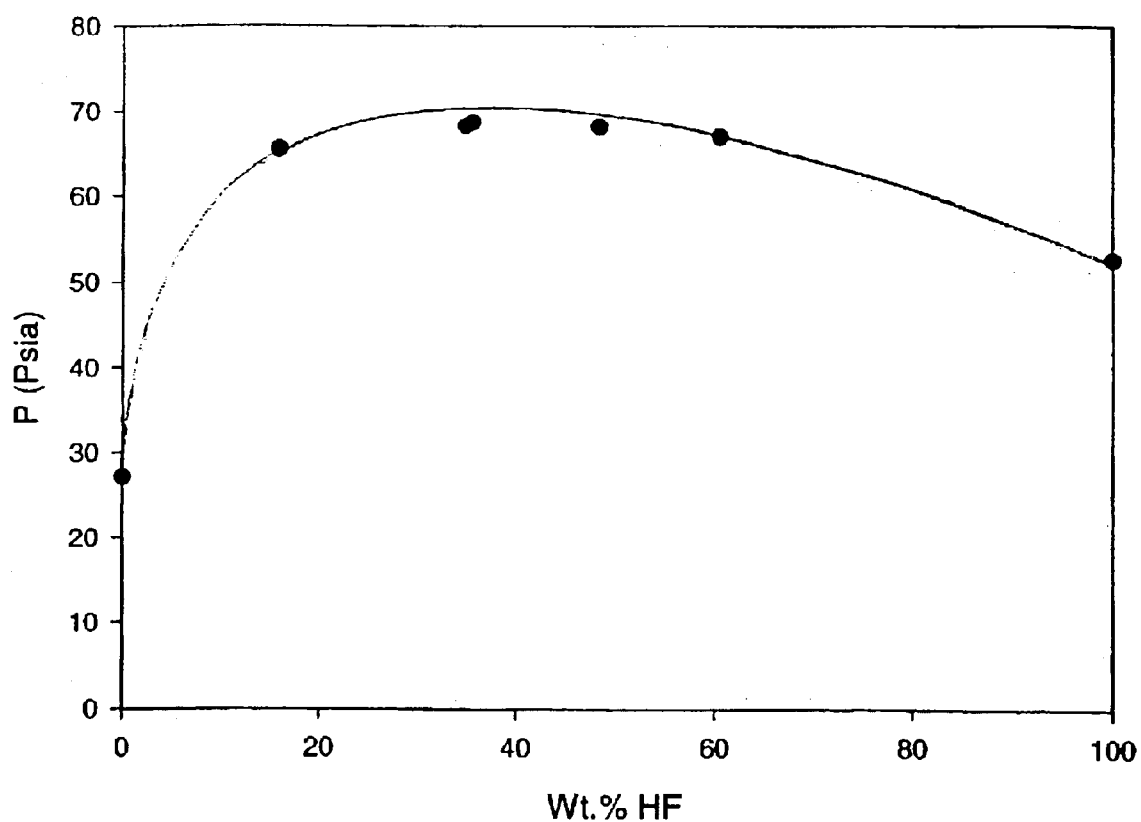

AZEOTROPE-LIKE COMPOSITION OF 1-CHLORO-1,3,3,3-TETRAFLUOROPROPANE AND HYDROGEN FLUORIDE

CROSS REFERENCE TO RELATED APPLICATION

This application is a divisional of U.S. patent application Ser. No. 09/768,416 (now U.S. Pat. No. 6,500, 795), incorporated by reference, which was filed with the USPTO on Jan. 24, 2001.

FIELD OF THE INVENTION

The present invention pertains to azeotropic and azeotrope-like compositions of 1-chloro-1,3,3,3-tetrafluoropropane (HCFC-244fa) and hydrogen fluoride.

BACKGROUND

In recent years there has been universal concern that completely halogenated chlorofluorocarbons (CFC's) might be detrimental to the Earth's ozone layer. Consequently, there is a worldwide effort to use fluorine-substituted hydrocarbons that contain fewer or no chlorine substituents. In this regard, 1,1,1,3,3-pentafluoropropane, a hydrofluorocarbon (HFC) having zero ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocaibons (HCFC's) or chlorofluorocarbons (CFC's) because they are not non-ozone depleting, but also they are also non-flammable, and non-toxic as compared to the chlorine containing compounds.

1,1,1,3,3-Pentaflutoropropane (HFC-245fa) is well known in the art as described in U.S. Pat. Nos. 5,496,866 and 5,574,192, both of which are incorporated by reference-herein in their entirety.

It has now been found that an intermediate in the production of substantially pure HFC-245fa, is an azeotropic or azeotrope-like mixture of 1-chloro-1,3,3,3-tetrafluoropropane (HCFC-244fa) and hydrogen fluoride. The azeotropic and azeotrope-like compositions find use not only as intermediates in the production of HFC-245fa, but they are additionally useful as nonaqueous etchant mixtures for etching semi conductors in the electronics industry, as well as compositions for removing surface oxidation from metals. In addition, the formation of an azeotropic or azeotrope-like composition of HCFC-244fa and hydrogen fluoride is useful in separating a mixture of HCFC-244fa and an impurity such as 1,1,1,3,3-pentachloropropane (HCC-240fa). When it is desired to separate a mixture of HCFC-244fa and an impurity, HF is added to form an azeotropic mixture of HCFC-244fa and hydrogen fluoride, and then the impurity is removed from the azeotropic mixture, such as by distillation, scrubbing or other known means.

SUMMARY OF THE INVENTION

In one embodiment, the invention provides an azeotropic composition consisting essentially of 1-chloro-1,3,3,3-tetrafluoropropane and hydrogen fluoride.

The invention further provides an azeotropic or azeotrope-like composition consisting essentially of from about 1 to about 75 weight percent hydrogen fluoride and from about 25 to about 99 weight percent 1-chloro-1,3,3,3-tetrafluoropropane, which composition has a boiling point of from about 30° C. to about 60° C. at a pressure of from about 10 psia to about 68 psia. In a preferred embodiment, the azeotropic or azeotrope-like compositions consist essentially of from about 15 to about 60 weight percent hydrogen fluoride and from about 40 to about 85 weight percent 1-chloro-1,2,2,2-tetrafluoropropane. In a more preferred embodiment, the azeotropic or azeotrope-like compositions consist essentially of from about 35 to about 40 weight percent hydrogen fluoride and from about 60 to about 65 weight percent 1-chloro-1,2,2,2-tetrafluoropropane.

In another embodiment, the invention provides a method of forming an azeotropic or azeotrope-like composition, which method comprises blending from about 1 to about 75 weight percent hydrogen fluoride and from about 25 to about 99 weight percent of 1-chloro-1,3,3,3-tetrafluoropropane, which composition has a boiling point of from about 30° C. to about 60° C. at a pressure of from about 10 psia to about 68 psia. In a preferred embodiment, the invention provides a method of forming an azeotropic or azeotrope-like composition, which method comprises blending from about 15 to about 60 weight percent hydrogen fluoride and from about 40 to about 85 weight percent of 1-chloro-1,3,3,3-tetrafluoropropane. In a more preferred embodiment, the invention provides a method of forming an azeotropic or azeotrope-like composition, which method comprises blending from about 35 to about 40 weight percent hydrogen fluoride and from about 60 to about 65 weight percent of 1-chloro-1,3,3,3-tetrafluoropropane.

In still another embodiment, the invention provides a process for removing 1-chloro-1,3,3,3-tetrafluoropropane from a mixture of 1-chloro-1,3,3,3-tetrafluoropropane and at least one impurity, which process comprises adding hydrogen fluoride to the mixture in an amount sufficient to form an azeotropic or azeotrope-like composition of 1-chloro-1,3,3,3-tetrafluoropropane and hydrogen fluoride, and thereafter separating the azeotropic composition from the impurity.

BRIEF DESCRIPTION OF THE DRAWINGS

FIG. 1 shows a plot of the vapor pressures of HCFC-244fa/HF mixtures as measured at 30° C.

FIG. 2 shows a plot of the vapor pressures of HCFC-244fa/fF mixtures as measured at 60° C.

DETAILED DESCRIPTION OF THE PREFERRED EMBODIMENT

In a method of preparing HCFC-244fa, precursor reagents are fluorinated with hydrogen fluoride. The reaction products of such precursors include HCFC-244fa, unreacted HF and other by-products. Upon removal of the by-products, a binary azeotrope or azeotrope-like composition of HCFC-244fa and HF is formed. This binary azeotrope or azeotrope-like composition is then available for separation into its component parts.

The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope-like composition means that the composition behaves like a true azeotrope in terms of its constant boiling characteristics and tendency not to fractionate upon boiling or evaporation. During boiling or evaporation, the liquid composition changes only slightly, if at all. This is in contrast with non-azeotrope-like compositions in which the liquid and vapor compositions change substantially during evaporation or condensation. One way to determine whether a candidate mixture is azeotrope-like within the meaning of this invention, is to distill a sample of it under conditions which would be expected to separate the mixture into its separate components. If the mixture is a non-azeotrope or non-azeotrope-like, the mixture will fractionate, i.e. separate into its various components with the lowest boiling component distilling off first, and so on. If the mixture is azeotrope-like, some finite amount of the first distillation cut will be obtained which contains all of the mixture components and which is constant boiling or behaves like a single substance. Another characteristic of azeotrope-like compositions is that there is a range of compositions containing the same components in varying proportions that are azeotrope-like. All such compositions are included by the term azeotrope-like as used herein. As an example, it is well known that at different pressures the composition of a given azeotrope will vary at least slightly as does the boiling point of the composition. Thus an azeotrope of two components represents a unique-type of relationship but with a variable composition depending on the temperature and/or pressure. As is well known in the art, the boiling point of an azeotrope will vary with pressure.

As used herein, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition comprising effective amounts of hydrogen fluoride and HCFC-244fa to form an azeotropic or azeotrope-like composition. By effective amount is meant an amount of each component which, when combined with the other component, results in the formation of an azeotrope or azeotrope-like mixture. The inventive compositions preferably are binary azeotropes that consist essentially of combinations of only hydrogen fluoride with HCFC-244fa.

In the preferred embodiment, the inventive composition contains from about 1 to about 75 weight percent HF, preferably from about 15 to about 60 weight percent and most preferably from about 35 to about 40 weight percent. In the preferred embodiment, the inventive composition contains from about 25 to about 99 HCFC-244fa, preferably from about 40 to about 85 weight percent and most preferably from about 60 to about 65 weight percent. The composition of the present invention has a boiling point of from about 30° C. to about 60° C. at a pressure of from about 10 psia to about 68 psia. An azeotropic or azeotrope-like composition having about 45±30 weight percent HF and about 45±5 weight percent HCFC-244fa has been found to boil at about 30° C. at 27 psia. An azeotropic or azeotrope-like composition of about 45±10 weight percent HF and about 65±5 weight percent HCFC-244fa has been found to boil at about 60° C. at 68 psia.

In another preferred embodiment of the invention, of HCFC-244fa may be removed from a mixture containing of HCFC-244fa and an impurity which may, for example, result from manufacturing steps in the preparation of HCFC-244fa. This is done by adding hydrogen fluoride to a mixture of HCFC-244fa and the impurity. Hydrogen fluoride is added to the mixture in an amount sufficient to form an azeotropic composition of HCFC-244fa and hydrogen fluoride, and thereafter the azeotropic composition is separated from the impurity, for example by distillation, scrubbing, or other art recognized separating means. Preferably, the impurity itself does not form a close-boiling azeotropic mixture with HCFC-244fa, hydrogen fluoride or a mixture of HCFC-244fa and hydrogen fluoride. As used herein, the term close-boiling azeotropic mixture means an azeotropic mixture having a boiling point within 10° C. of the azeotropic mixture of the invention.

The following non-limiting examples serve to illustrate the invention.

EXAMPLE 1

50 g of 1-chloro-1,3,3,3-tetrafluoropropane (HCFC-244fa) is dissolved in 50 g of HF to form a heterogeneous mixture. The vapor of the mixture at 30° C. is 27 psia.

EXAMPLE 2

65 g of 1-chloro-1,3,3,3-tetrafluoropropane (HCFC-244fa) is dissolved in 35 g of HF to form a heterogeneous mixture. The vapor pressure of the mixture at 60° C. is 67 psia.

EXAMPLE 3

Binary compositions containing solely 1-chloro-1,3,3,3-tetrafluoropropane (HCFC-244fa) and HF are blended to form various heterogeneous mixtures. The vapor pressures of the mixtures are measured at 30° C. and 60° C. and the following results are noticed.

Table 1 shows the vapor pressure measurement of HCFC-244fa and HF as a function of composition of weight percent HF at two constant temperatures of 30° C. and 60° C. From this table it is observed that at 30° C. the composition at which the vapor pressure is maximum is between about 15 and about 60 weight percent HF. At 60° C., the composition at which the vapor pressure is maximum at about 35 weight percent HF or between about 15 and about 48 weight percent HF.

TABLE I

| WEIGHT PERCENT HF | PRESSURE (PSIA) | |
| --- | --- | --- |
| | 30° C. | 60° C. |
| 0.0 | 10.04 | 27.14 |
| 15.69 | 26.95 | 56.42 |
| 34.65 | 26.95 | 68.25 |
| 48.21 | 27.41 | 68.16 |
| 60.50 | 27.41 | 67.06 |
| 100.0 | 21.71 | 52.71 |

The data also show that the vapor pressure of mixtures of HCFC-244fa and HF is higher, at all indicated blend proportions, than HCFC-244fa and HF alone, i.e. as indicated in the first and last rows when HF is 0.0 wt. % and HCFC-244fa is at 100.0 wt. % as well as when HFC-244fa is at 0.0 wt. % and HF is at 100.0 wt. %.

The azeotropic compositions of HFC-244fa and HF may also be verified by vapor-liquid equilibrium (VLE) measurements. The liquid and vapor of the mixtures are sampled at about 35±5 weight percent HF at about 30° C. and 60° C. At 60° C. it is determined that the liquid and vapor compositions are about the same at about 35±5 weight percent HF. At 30° C. it is determined that the liquid and vapor compositions are about the same at about 40±10 weight percent HF.

TABLE 2

| TEMPERATURE | PRESSURE | COMPOSITIONS (WEIGHT PERCENT HF, ±3%) | |
| --- | --- | --- | --- |
| (° C.) | (Psia) | LIQUID | VAPOR |
| 30.44 | 26.96 | 35.40 | 43.44 |
| 60.42 | 68.73 | 35.38 | 36.37 |

A comparison of the data from Tables 1 and 2 indicates that the vapor-liquid equilibrium results from Table 2 are in agreement with the vapor pressure measurements of Table 1. The data from Table 1 are shown in graphic form in FIGS. 1 and 2.

What is claimed is:

1. A method of forming an azeotropic or azeotrope-like composition which method consists essentially of blending from about 1 to about 75 weight percent hydrogen fluoride and from about 25 to about 99 weight percent 1-chloro-1,3,3,3-tetrafluoropropane, which composition has a boiling point of from about 30° C. to about 60° C. at a pressure of from about 10 psia to about 68 psia.

2. The method of claim 1 wherein the composition consists of hydrogen fluoride and 1-chloro-1,3,3,3-tetrafluoropropane.

3. The method of claim 1 wherein the hydrogen fluoride in present in an amount of from about 15 to about 60 weight percent.

4. The method of claim 1 wherein the hydrogen fluoride in present in an amount of from about 35 to about 45 weight percent.

5. The method of claim 1 wherein the composition has a boiling point of from about 30° C. at a pressure of about 27 psia.

6. The method of claim 1 wherein the composition has a boiling point of from about 60° C. at a pressure of about 68 psia.

7. A process for removing 1-chloro-1,3,3,3-tetrafluoropropane from a mixture of 1-chloro-1,3,3,3-tetrafluoropropane and at least one impurity, which process comprises adding hydrogen fluoride to the mixture in an amount sufficient to form an azeotropic or azeotrope-like composition of the 1-chloro-1,3,3,3-tetrafluoropropane and the hydrogen fluoride, and thereafter separating the azeotropic composition from the impurity.

8. The process of claim 7 wherein the impurity does not form a close-boiling azeotropic mixture with 1-chloro-1,3,3,3-tetrafluoropropane, hydrogen fluoride or a mixture of 1-chloro-1,3,3,3-tetrafluoropropane and hydrogen fluoride.

9. The process of claim 7 wherein the impurity comprises a halocarbon.

10. The process of claim 7 wherein the impurity is miscible with 1-chloro-1,3,3,3-tetrafluoropropane.

11. The process of claim 7 wherein the impurity is 1,1,1,3,3-pentachloropropane.

12. The process of claim 7 wherein the separating is conducted by distillation.

13. The process of claim 7 wherein the azeotropic composition consists essentially of from about 1 to about 75 weight percent hydrogen fluoride and from about 40 to about 99 weight percent 1-chloro-1,3,3,3-tetrafluoropropane.

14. The process of claim 7 wherein the azeotropic composition consists essentially of from about 15 to about 60 weight percent hydrogen fluoride.

15. The process of claim 7 wherein the azeotropic composition consists essentially of from about 35 to about 40 weight percent hydrogen fluoride.

* * * * *